United States Patent
Benz et al.

[19]

[11] Patent Number: 5,913,881
[45] Date of Patent: Jun. 22, 1999

[54] METALLIC HOUSING FOR IMPLANT WITH RECESSES FOR EDDY CURRENT REDUCTION

[75] Inventors: Hans-Thomas Benz, Buckenhof; Gerhard Fischer, Unterschleissheim, both of Germany

[73] Assignee: Biotronik Mess-und Therapiegeraete GmbH & Co., Ingenieurbüro Berlin, Germany

[21] Appl. No.: 08/956,470

[22] Filed: Oct. 23, 1997

[30] Foreign Application Priority Data

Oct. 23, 1996 [DE] Germany ............... 196 45 371

[51] Int. Cl.⁶ .................................................. A61N 1/375
[52] U.S. Cl. ................................................................ 607/36
[58] Field of Search ................... 607/36, 30, 32, 607/119, 4, 9, 33; 128/903

[56] References Cited

U.S. PATENT DOCUMENTS

| | | | |
|---|---|---|---|
| 3,598,128 | 8/1971 | Chardack | 607/36 |
| 3,735,766 | 5/1973 | Bowers et al. | 607/36 |
| 4,006,748 | 2/1977 | Schulman | 607/36 |
| 4,041,955 | 8/1977 | Kelly et al. | |
| 4,369,791 | 1/1983 | Friedman | 607/36 |
| 4,949,719 | 8/1990 | Pless et al. | 607/4 |
| 4,991,582 | 2/1991 | Byers et al. | |
| 5,264,843 | 11/1993 | Silvian | |
| 5,480,416 | 1/1996 | Garcia et al. | 607/36 |
| 5,529,579 | 6/1996 | Alt et al. | 607/36 |
| 5,658,321 | 8/1997 | Fayram et al. | 607/36 |

FOREIGN PATENT DOCUMENTS 2720011  8/1985  Germany.

*Primary Examiner*—William E. Kamm
*Assistant Examiner*—Kennedy J. Schaetzle
*Attorney, Agent, or Firm*—Venable; George H. Spencer; Robert Kinberg

[57] ABSTRACT

An implant for implanting into human tissue includes a hermetically sealed, metallic housing for enclosing electronic means inside the housing for a high-frequency, telemetric information transfer between a programming device and the implant. The implant additionally includes a head for connecting a stimulation line. The housing comprises a metallic wall including groove-shaped recesses arranged at least on an inside of the metallic wall and which reduce a thickness of the metallic wall so that in a region of the recesses on the housing wall a material thickness does not fall below that which is necessary under operating conditions to ensure that the housing is impermeable to fluids.

25 Claims, 6 Drawing Sheets

METALLIC HOUSING FOR IMPLANT WITH RECESSES FOR EDDY CURRENT REDUCTION

BACKGROUND OF THE INVENTION

The invention concerns an implant for implanting into human tissue of the type including a hermetically sealed, metallic housing for enclosing electronic means inside the housing for a high-frequency, telemetric information transfer between a programming device and the implant, the implant including a head for connecting a stimulation line. Such an implant is known from German patent document DE 27 20 011 C2.

The contact between the electronic components and the salt-containing and therefore conductive body fluid must be avoided for implants that can be implanted into human tissue, e.g. a pacemaker, as this will otherwise lead to signs of corrosion and electrical malfunctions of the pacemaker. A hermetically sealed metal housing is provided for this, which protects the sensitive electronic componentry of the pacemaker to a sufficient degree. However, such metal capsules have the disadvantage of leading to a more or less strong screening of magnetic and electromagnetic alternating fields during the pacemaker operation, which fields are used for an energy or signal input or discharge into or from the pacemaker. On the one hand, this energy loss, which is essentially caused by eddy currents, makes itself felt by a heating up of the housing frequently perceived as physiologically troublesome by the patient while, on the other hand, it requires a larger amount of energy for a secure signal transmission over a specific distance. This constitutes a high stress, particularly for the energy storage device present in the pacemaker, which has the disadvantage of causing a shortening of the discharge time for the energy storage device used. The eddy current losses increase with an increase in the frequency and limit the range of the telemetric data transmission in addition to the data throughput rate.

The conductivity and thickness of the housing material determine the size of the eddy currents. The thicker the material and the higher its conductivity, the larger the eddy currents caused by telemetric transmissions.

The above-mentioned document DE 27 20 011 C2 discloses a rechargeable pacemaker, having a smooth, polished housing wall composed of a biocompatible material and a uniform thickness in the range of 0.05 mm to 0.13 mm. The energy input for charging up the battery inside the housing is supplied to the pacemaker via an external, magnetic alternating field, wherein the energy losses that lead to a troublesome warming up of the housing caused by eddy currents, must be reduced through specific dimensioning of the measurements. That is the reason why the quotient for the material strength and specific electrical resistance of the metallic material used for the pacemaker housing is selected to be below a predetermined limit value.

Since it is only the material strength of the housing wall that determines this quotient for a selected, biocompatible metallic material, the use of this solution is limited in a disadvantageous way. These limits are basically predetermined by a minimum wall thickness of the housing, which is necessary for the safe operation of the pacemaker, meaning mechanical stability and imperviousness to the body fluid surrounding the pacemaker.

SUMMARY OF THE INVENTION

It is an object of the invention to provide an implant of the generic type as mentioned above, having a housing design, which permits a further lowering of the energy losses during a signal transmission into or from the implant while having a sufficient mechanical stability for a secure operation of the implant.

The above and other objects are accomplished according to the invention by the provision of an implant for implanting into human tissue, including a hermetically sealed, metallic housing for enclosing electronic means inside the housing for a high-frequency, telemetric information transfer between a programming device and the implant, the implant including a head for connecting a stimulation line, wherein the housing comprises a metallic wall including groove-shaped recesses arranged at least on an inside of the metallic wall and which reduce a thickness of the metallic wall so that in a region of the recesses on the housing wall a material thickness does not fall below that which is necessary under operating conditions to ensure that the housing is impermeable to fluids.

The invention reflects the realization that it is possible in an easy and at the same time advantageous way to reduce the buffering effect of a metallic, hermetically sealed housing for electromagnetic alternating fields with respect to the telemetric signal transmission into or from an implant, necessary for the programming, if the housing wall is provided with a structure that counters in particular the effect of an undisturbed expansion of eddy currents, induced in the housing wall during the signal transmission. On the one hand, this structuring relates to the mechanical design of the wall for reducing the thickness and, on the other hand, to a change in the metallic structure of the wall material for reducing the electrical conductivity.

In accordance with the invention, the housing of the implant, preferably designed as a pacemaker, has a wall with groove-shaped recesses. These recesses form housing regions with a reduced metallic wall strength that are enclosed by regions with a higher wall strength and thus have a high electrical resistance owing to their geometry, which reduces the size of the induced eddy currents. The recesses are located on the inside of the housing wall.

The groove-shaped recesses in the housing wall are filled with an electrically non-conductive, mechanically solid material to essentially increase the mechanical stability of the housing wall, reduced as a result of the groove insertion, once more to the necessary value for a secure operation of the pacemaker.

According to a favorable modification, the filler material in the groove-shaped recesses consists of a plastic material, preferably an epoxy resin, or a polyester resin which is biocompatible and resistant to the body fluid surrounding the implanted pacemaker.

Owing to the adhesive effect, the use of an epoxy resin advantageously secures a fixed connection between the filler material and the side walls of the groove-shaped recesses, which is necessary for the mechanical stability of the pacemaker housing wall.

In accordance with a preferred embodiment of the invention, the grooves have a parallelepiped shape, are uniformly distributed and extend essentially parallel to each other, crosswise to the longitudinal axis of the pacemaker head and across the total length of the respective broadside of the housing. The edge regions of the parallelepiped grooves have a rounded design to avoid local extreme values for mechanical stresses and to make it easier to completely fill the recesses with a plastic material.

In accordance with a favorable modification of the invention, the recesses in the housing wall consist of parallelepiped grooves with ends having a semi-cylindrical design, wherein several, preferably two, groove segments of a different length but located on the same axis form a row, extending crosswise to the longitudinal axis of the head. A plurality of rows formed by groove-shaped recesses are respectively arranged parallel to each other on the broadsides of the pacemaker housing. It is advantageous if the position of the longer groove segment, for example, is changed from row to row so as to improve the mechanical stability of the housing wall weakened by the recesses.

In accordance with another advantageous embodiment of the invention, the groove-shaped recesses exist only in the wall region of the pacemaker housing, behind which the electronic componentry necessary for the signal transmission into or from the pacemaker is positioned on the inside of the housing. This technologically favorable embodiment is possible since the exact position of the pacemaker can be determined prior to the signal transmission and since the programming heads of the electronic units used to program a pacemaker have only a relatively small size.

In accordance with additional modifications of the invention, the groove-shaped recesses exist either on the inside and the outside or only on the outside of the housing wall.

According to the preferred embodiment, the material strength of the pacemaker housing wall is reduced in the groove-shaped recesses by at least 60%, preferably 80%, as compared to the wall regions without grooves.

In accordance with another advantageous embodiment of the invention, the material used for the housing wall, which is formed into a sheet metal, displays localized changes in the material structure, caused by selective oxidation through oxygen implantation, localized alloy formation or localized implantation of impurities, thereby leading to a reduction in the electrical conductivity of the implant housing. An additional reduction in the eddy currents is possible in this way.

BRIEF DESCRIPTION OF THE DRAWINGS

Other advantageous modifications of the invention are shown in more detail in the following with the aid of figures, together with the description of the preferred embodiment of the invention. Shown are in.

DETAILED DESCRIPTION OF THE INVENTION

Figure 1:
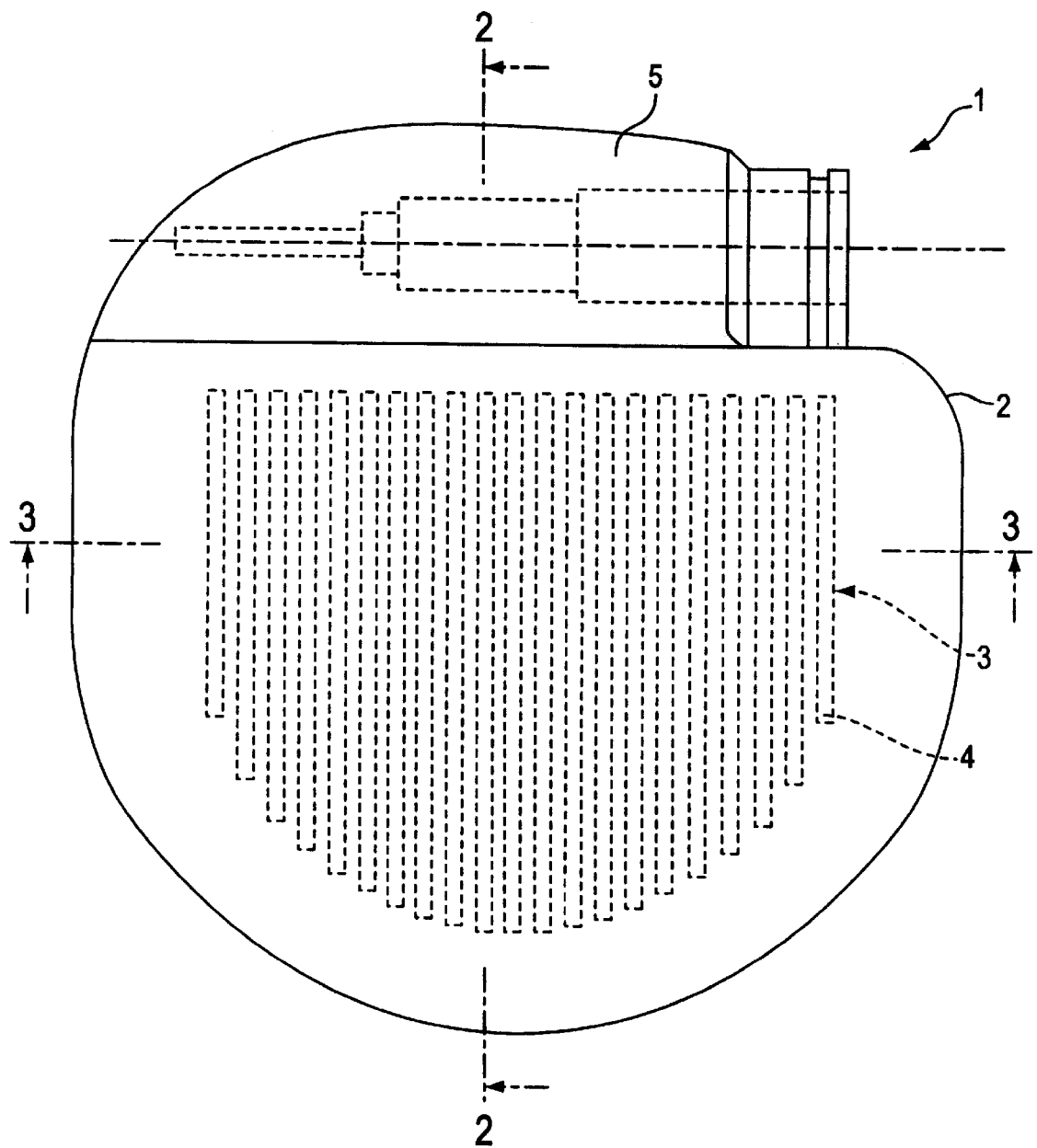
FIG. 1 a view from the side of a preferred embodiment of the invention.

In FIG. 1, a pacemaker 1 is shown diagrammatically in a view from the side. The cup-shaped housing 2 is closed off with a head 5, which contains a tip jack 10 for connecting a stimulation line (not shown). Groove-shaped recesses 3 that extend perpendicular to the longitudinal axis 9 of head 5 are provided at the broadsides of housing 2. The groove-shaped recesses 3 on the inside of the housing wall have a parallelepiped shape, extend parallel to each other, and are arranged such that they are distributed evenly over the total broadside of housing 2. With the relatively low material strength of the housing wall, the groove-shaped recesses can be produced through shaping without cutting of the housing halves or through laser processing.

An electrically non-conducting filler material 4 is placed into the groove-shaped recesses 3, which fills the grooves 3 completely and forms an adhesive bond with the groove walls. The filler material 4 is preferably a plastic filler material, and more preferably is composed of an epoxy resin or polyester resin that adheres to the groove wall. The mechanical instability caused by inserting grooves 3 into the housing wall 2 is almost completely compensated by the plastic filler material 4. The housing 2 of pacemaker 1 is gas-impermeable, and the forming of eddy currents in the housing wall 2 during the signal transmission from and to the pacemaker is suppressed almost completely.

Figure 2:
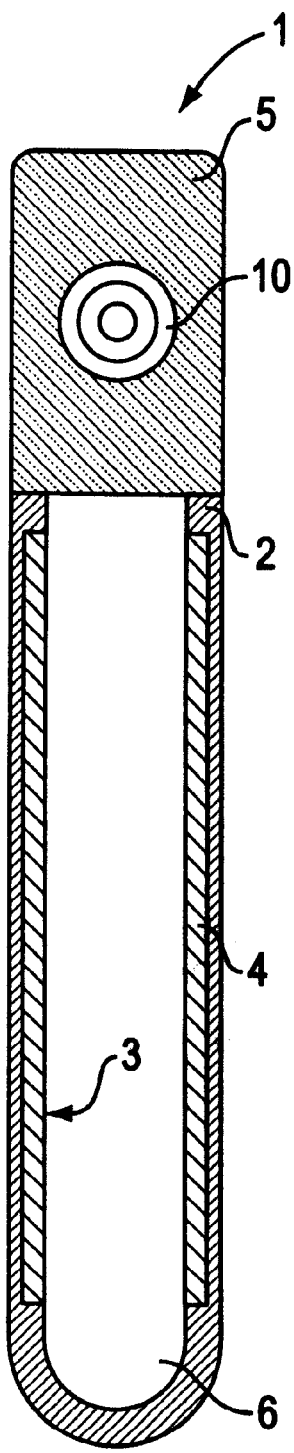
FIG. 2 the illustrated view of a section along the line 2—2 according to FIG. 1.
Figure 3:
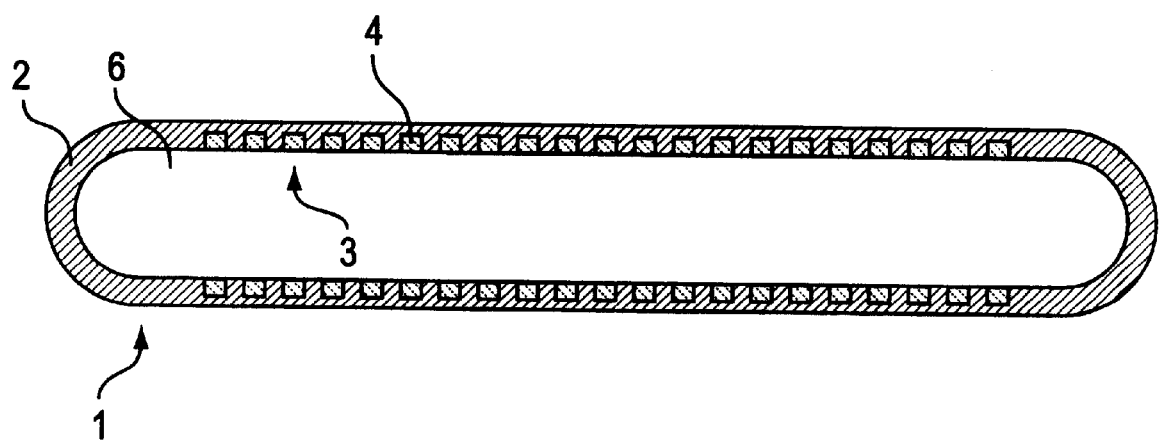
FIG. 3 the illustrated view of a section along the line 3—3 according to FIG. 1.

The illustration in FIGS. 2 and 3 shows the shape of the groove-shaped recesses 3 in the wall for the housing 2. The recesses 3 provided on the inside of the housing wall have a parallelepiped shape and rounded edge regions. As a result of this, local extreme values for mechanical stresses are avoided, and it is easier to fill the recesses completely with plastic material.

An energy storage device (compare the position 7 in FIG. 6) and electronic means for a high-frequency information transmission (compare the position 8 in FIG. 6) from a programming device to the implant and from the implant to the programming device are arranged on the housing inside area 6.

Figure 4:
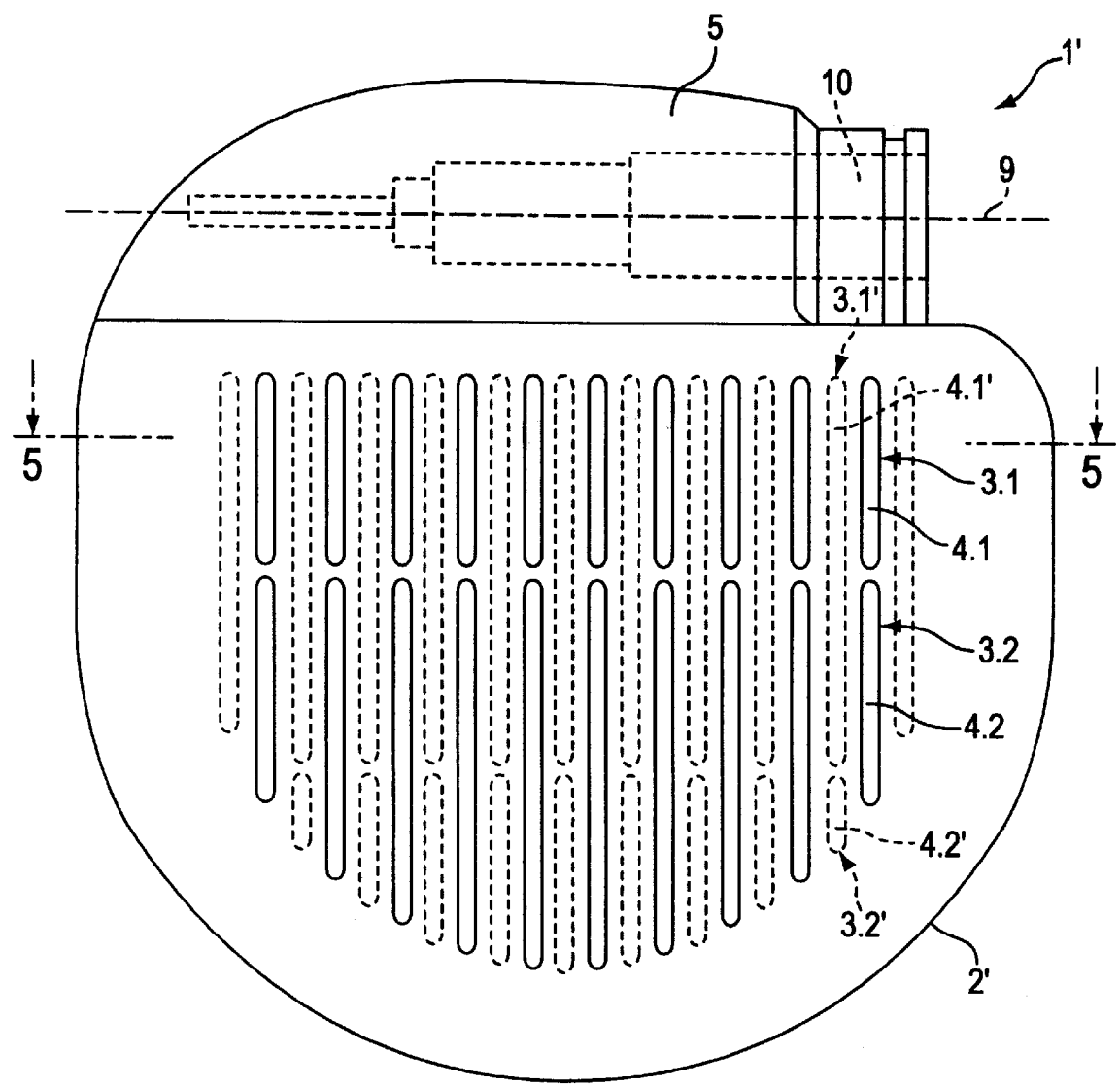
FIG. 4 A view from the side of another advantageous embodiment of the invention.
Figure 5:
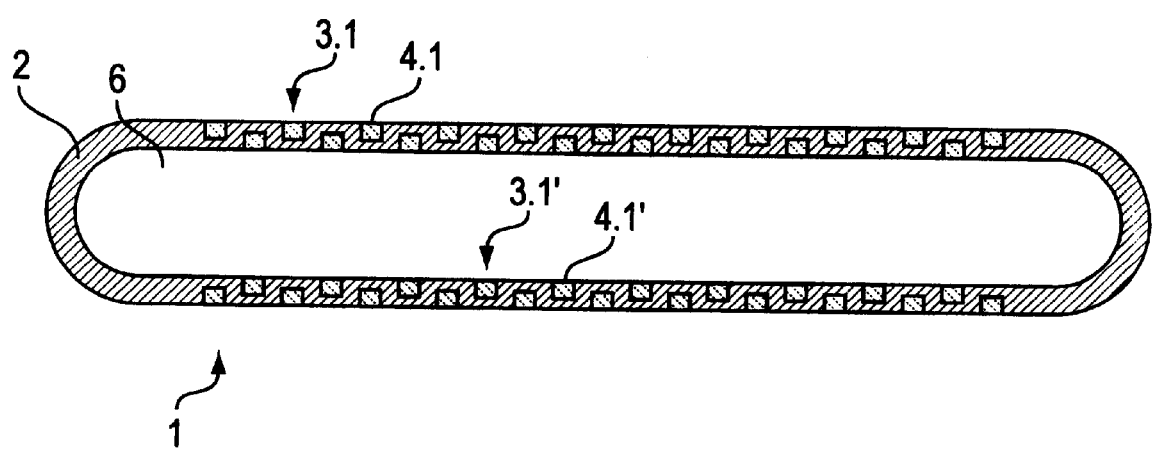
FIG. 5 the view of a section along the line 5—5according to FIG. 4.

The housing 2' of a pacemaker 1', shown in FIGS. 4 and 5 as a diagram from the side and as a sectional view, has groove-shaped recesses in the wall of the housing broadsides, which are arranged alternately on the inside and outside of the housing wall and are divided into differently long segments 3.1 and 3.2 or 3.1' and 3.2'.

The segments 3.1 and 3.2 or 3.1' and 3.2' are located on the same axis and their ends have a semi-cylindrical shape. All edge areas are rounded off. The position of the longer groove segments 3.2 and 3.2' is advantageously changed from row to row to improve the mechanical stability of the housing wall that is weakened by the recesses 3.1 and 3.2 or 3.1' and 3.2'. In the same way as the embodiment of the invention shown in FIG. 1, the groove-shaped recesses 3.1 and 3.2 or 3.1' and 3.2' respectively contain an epoxy resin filler material 4.1, 4.2, 4.1', 4.2', so that the outside wall of the pacemaker housing has a uniform, smooth surface and has essentially the same mechanical stability as a wall without grooves.

Figure 6:
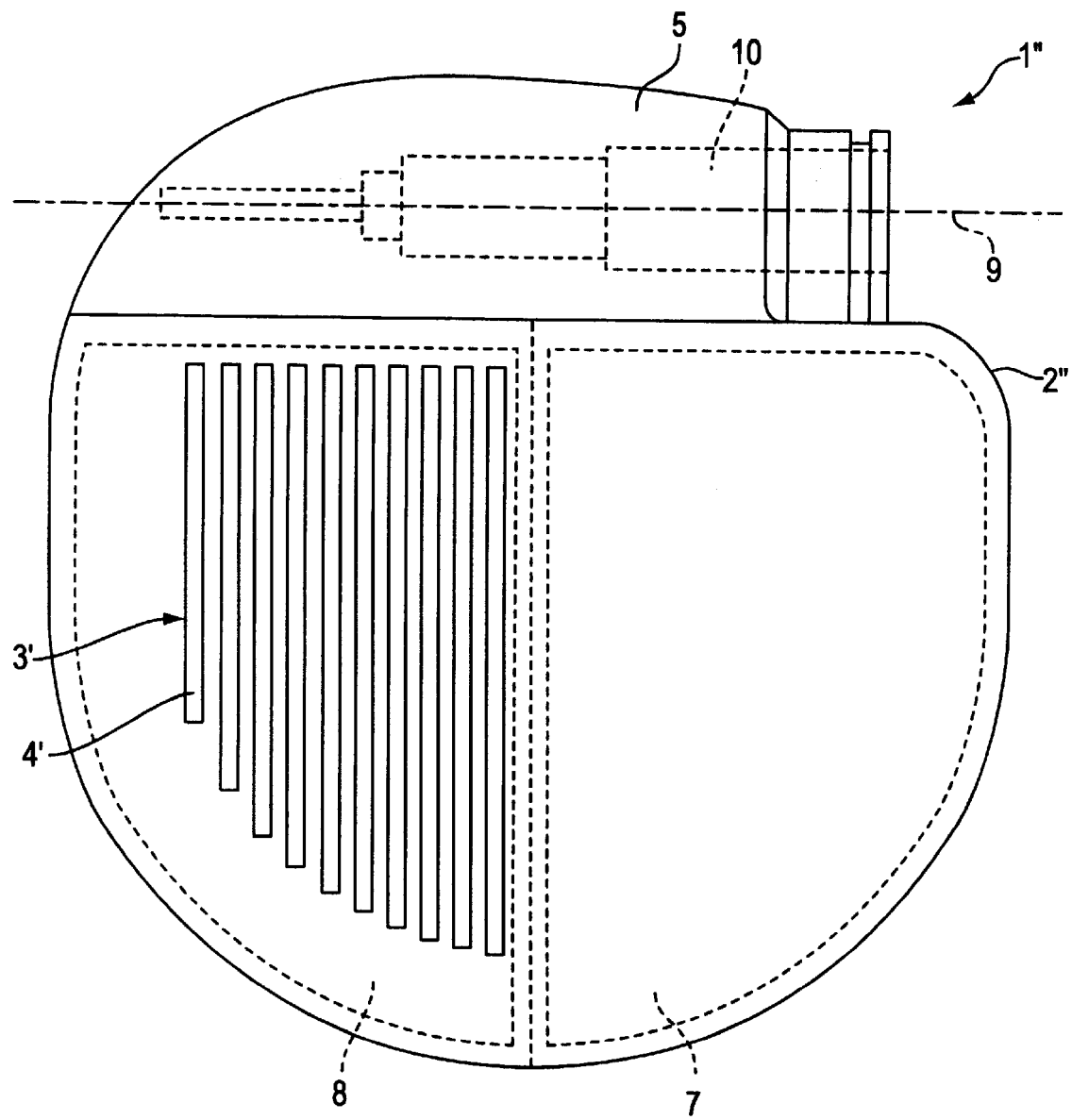
FIG. 6 a favorable modification of the invention in a view from the side.

The embodiment 1" of the invention, shown in FIG. 6, comprises a housing 2" with a grooved area 3 on the wall outside, but only in the housing 2" regions behind which the electronic means 8 are located that are used for the high-frequency telemetric information transfer from a programming device to the pacemaker 1" and from the pacemaker to the programming device. The shape of the groove-shaped recesses 3' and their filler material 4' corresponds to the above-described embodiments.

What is claimed is:

1. An implant for implanting into human tissue, comprising:
   a hermetically sealed, metallic housing for enclosing electronic means inside the housing for a high-frequency, telemetric information transfer between a programming device and the implant, the implant including a head for connecting a stimulation line, wherein the housing comprises a metallic wall including groove-shaped recesses arranged at least on an inside of the metallic wall and which reduce a thickness of the metallic wall so that in a region of the recesses on the housing wall a material thickness does not fall below that which is necessary under operating conditions to ensure that the housing is impermeable to fluids.

2. The implant according to claim 1, wherein the groove-shaped recesses are additionally arranged on an outside wall of the housing.

3. The implant according to claim 1, wherein the groove-shaped recesses are arranged on a wall region of the housing which covers a telemetric route of the electronic means.

4. The implant according to claim 1, further including a filler material of an electrically non-conductive material filling the groove-shaped recesses.

5. The implant according to claim 4, wherein the filler material comprises a plastic material.

6. The implant according to claim 5, wherein the plastic filler material comprises polyester resin.

7. The implant according to claim 1, wherein the groove-shaped recesses extend essentially parallel to each other and crosswise to a longitudinal axis of the head.

8. The implant according to claim 7, wherein the groove-shaped recesses are divided respectively into two segments of different length that are positioned on the same axis to form respective rows.

9. The implant according to claim 8, wherein a sequence of the segments with unequal length in each row changes from one row to an adjacent row of the recesses.

10. The implant according to claim 1, wherein a strength of the metallic wall is reduced by at least 60% in the region of the recesses.

11. The implant according to claim 1, wherein the groove-shaped recesses extend over a total broadside of the housing and are distributed evenly.

12. The implant according to claim 1, wherein the groove-shaped recesses have an essentially parallelepiped shape.

13. The implant according to claim 12, wherein the groove-shaped recesses have end regions with a semi-cylindrical shape.

14. The implant according to claim 1, wherein the housing includes material regions of reduced electrical conductivity, caused by one of localized oxygen implantation, localized alloy-formation and localized impurities inserted into the structure.

15. The implant according to claim 1, wherein the housing comprises titanium.

16. The implant according to claim 1, wherein the implant comprises a pacemaker.

17. The implant according to claim 1, wherein a strength of the metallic wall is reduced by at least 80% in the region of the recesses.

18. An implant for implanting into human tissue, comprising:

a hermetically sealed, metallic housing for enclosing electronic means inside the housing for a high-frequency, telemetric information transfer between a programming device and the implant, the implant including a head for connecting a stimulation line, wherein the housing comprises: a metallic wall including groove-shaped recesses arranged at least on one of an inside and outside of the metallic wall and which reduce a thickness of the metallic wall so that in a region of the recesses on the housing wall a material thickness does not fall below that which is necessary under operating conditions to ensure that the housing is impermeable to fluids; and a material filling the recesses to effectively compensate for a mechanical instability caused by the recesses.

19. The implant according to claim 18, wherein the material filling the recesses comprises a plastic material.

20. The implant according to claim 18, wherein the plastic material comprises polyester resin.

21. The implant according to claim 18, wherein the plastic material comprises epoxy resin.

22. The implant according to claim 18, wherein the material completely fills the recesses.

23. An implant for implanting into human tissue, comprising:

a hermetically sealed, metallic housing for enclosing electronic means inside the housing for a high-frequency, telemetric information transfer between a programming device and the implant, the implant including a head for connecting a stimulation line, wherein the housing comprises a metallic wall including groove-shaped recesses arranged in parallel rows at least on one of an inside and outside of the metallic wall and which reduce a thickness of the metallic wall so that in a region of the recesses on the housing wall a material thickness does not fall below that which is necessary under operating conditions to ensure that the housing is impermeable to fluids, and wherein the groove-shaped recesses are divided respectively into two segments of different length that are positioned on the same axis in each row.

24. The implant according to claim 23, wherein a sequence of the segments with unequal length in each row changes from one row to an adjacent row of the recesses.

25. The implant according to claim 23, wherein the head has a longitudinal axis and the parallel rows of recesses extend crosswise to the longitudinal axis of the head.

* * * * *